US00PP36827P2

(12) United States Plant Patent
Star

(10) Patent No.: US PP36,827 P2
(45) Date of Patent: Jul. 15, 2025

(54) ***SANGUISORBA* PLANT NAMED 'Black Dream Select'**

(50) Latin Name: *Sanguisorba officinalis*
Varietal Denomination: Black Dream Select

(71) Applicant: Jan Star, Rijnsburg (NL)

(72) Inventor: Jan Star, Rijnsburg (NL)

(73) Assignee: IP—PLANTS B.V., Sassenheim (NL)

( * ) Notice: Subject to any disclaimer, the term of this patent is extended or adjusted under 35 U.S.C. 154(b) by 0 days.

(21) Appl. No.: 19/048,875

(22) Filed: Feb. 8, 2025

(30) Foreign Application Priority Data

Oct. 17, 2024 (QZ) ..... PBR 20242410

(51) Int. Cl.
*A01H 5/02* (2018.01)
*A01H 6/74* (2018.01)

(52) U.S. Cl.
USPC ..... Plt./263.1
CPC ..... *A01H 6/74* (2018.05); *A01H 5/02* (2013.01)

(58) Field of Classification Search
USPC ..... Plt./263.1
See application file for complete search history.

(56) References Cited

U.S. PATENT DOCUMENTS

PP33,601 P2 * 11/2021 Star ..... A01H 6/74
Plt./263.1

* cited by examiner

*Primary Examiner* — Karen M Redden
(74) *Attorney, Agent, or Firm* — Penny J. Aguirre

(57) ABSTRACT

The new cultivar of *Sanguisorba* plant named 'Black Dream Select' that is characterized by its unique flower colors; dark purple-red to brown-black in color, its blooming period from July to August, and its equal height of the stems and flowers, between 1 to 1.25 m in height.

3 Drawing Sheets

Botanical classification: *Sanguisorba officinalis*.
Variety denomination: 'Black Dream Select'.

CROSS-REFERENCE TO A RELATED APPLICATION

This application claims priority to European Community Plant Variety Office (CPVO) Plant Breeder's Rights Application No. 2024/2410 filed on Oct. 17, 2024, under 35 U.S.C. 119(f), the entire contents of which is incorporated by reference herein. The information for the Plant Breeders' Rights application was received directly from the Inventor.

BACKGROUND OF THE INVENTION

The present invention relates to a new and distinct cultivar of *Sanguisorba officinalis* and will be referred to hereafter by its cultivar name, 'Black Dream Select'. 'Black Dream Select' represents a new burnet, an herbaceous perennial grown for landscape use.

'Black Dream Select' was selected by the Inventor as a seedling in a trial garden in Rijnsburg, The Netherlands in August of 2020. The seedling arose from seed sown in 2019 from open-pollination in 2018 of unnamed and unpatented plants of *Sanguisorba officinalis* in the Inventor's breeding program. The seeds were pooled after collection and therefore the exact parents are unknown.

Asexual propagation of the new cultivar was first accomplished by division in November 2020 by the inventor in Rijnsburg, The Netherlands. Asexual propagation by division and tissue culture using meristematic tissue has determined that the new cultivar is stable and reproduced true to type in successive generations.

SUMMARY OF THE INVENTION

The following traits have been repeatedly observed and represent the characteristics of the new cultivar. These attributes in combination distinguish 'Black Dream Select' as a unique cultivar of *Sanguisorba*.

1. 'Black Dream Select' exhibits unique flower colors; dark purple-red to brown-black in color.
2. 'Black Dream Select' exhibits a blooming period from July to August.
3. 'Black Dream Select' exhibits an equal height of the stems and flowers, between 1 to 1.25 m in height.

'Black Dream Select' can be most closely compared to *Sanguisorba officinalis* cultivars 'Red Dream' (U.S. Plant Pat. No. 32,441) and 'Big Dream' (U.S. Plant Pat. No. 33,601). Both are similar to 'Black Dream Select' in having inflorescence that re similar in shape. 'Red Dream' differs from 'Black Dream Select' in having dark red colored inflorescences that are larger and longer in length, darker green foliage, less flowers, and stems that are taller in height. 'Big Dream' differs from 'Black Dream Select' in having grey-purple colored flowers that are larger and longer in length, darker green foliage, leaves that are larger in size, less flowers, and stems that are taller in height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Holex, Vision Pictures, and Triangle Nursery.

BRIEF DESCRIPTION OF THE DRAWINGS

The accompanying color photographs illustrate the overall appearance and distinct characteristics of the new *Sanguisorba*. The photographs were taken of a one-year-old plant of the new cultivar as field grown outdoors in Rijnsburg, The Netherlands.

The photograph in FIG. 1 illustrates the overall habit and appearance of 'Black Dream Select' in bloom.

Figure 1:
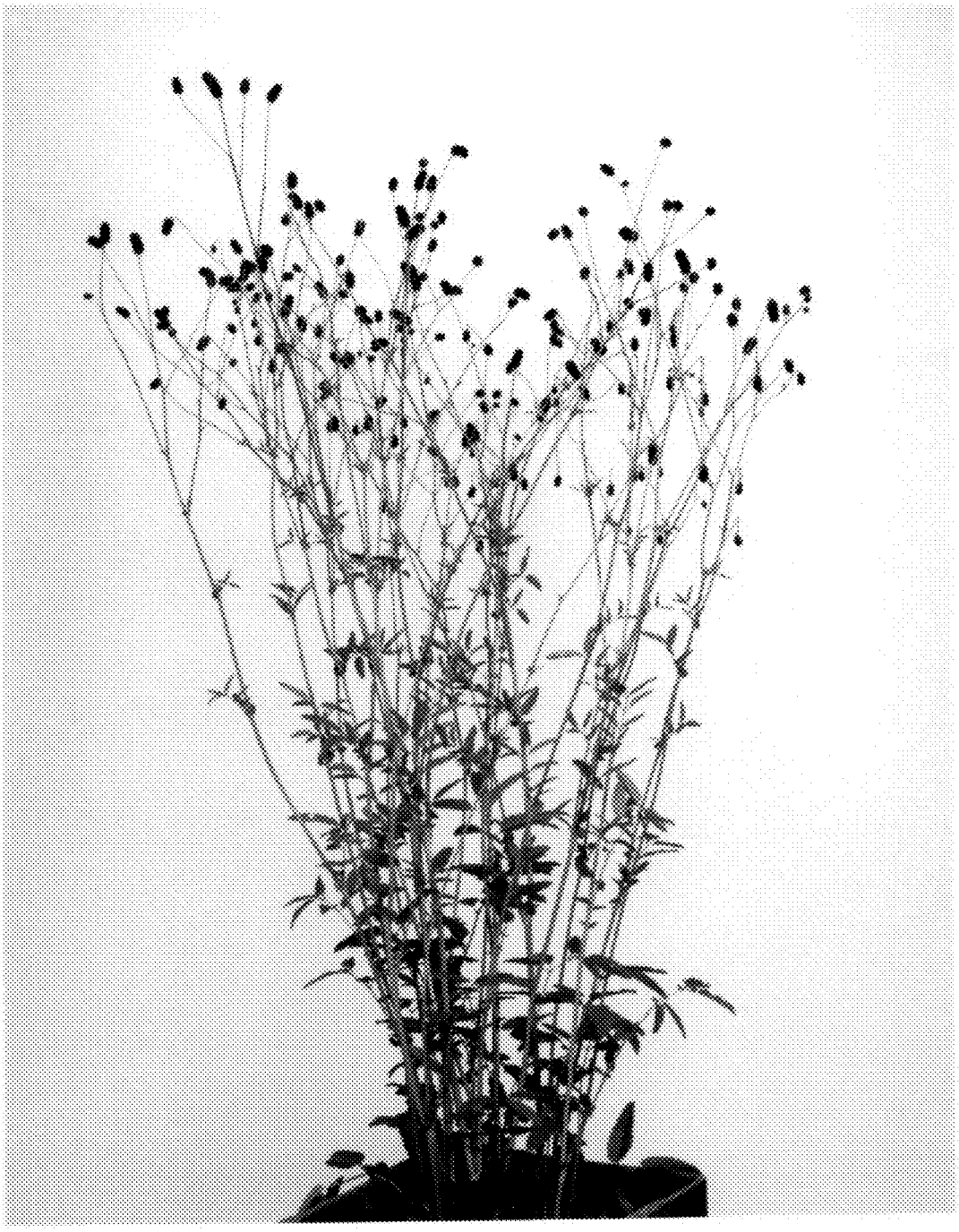
Figure 2:
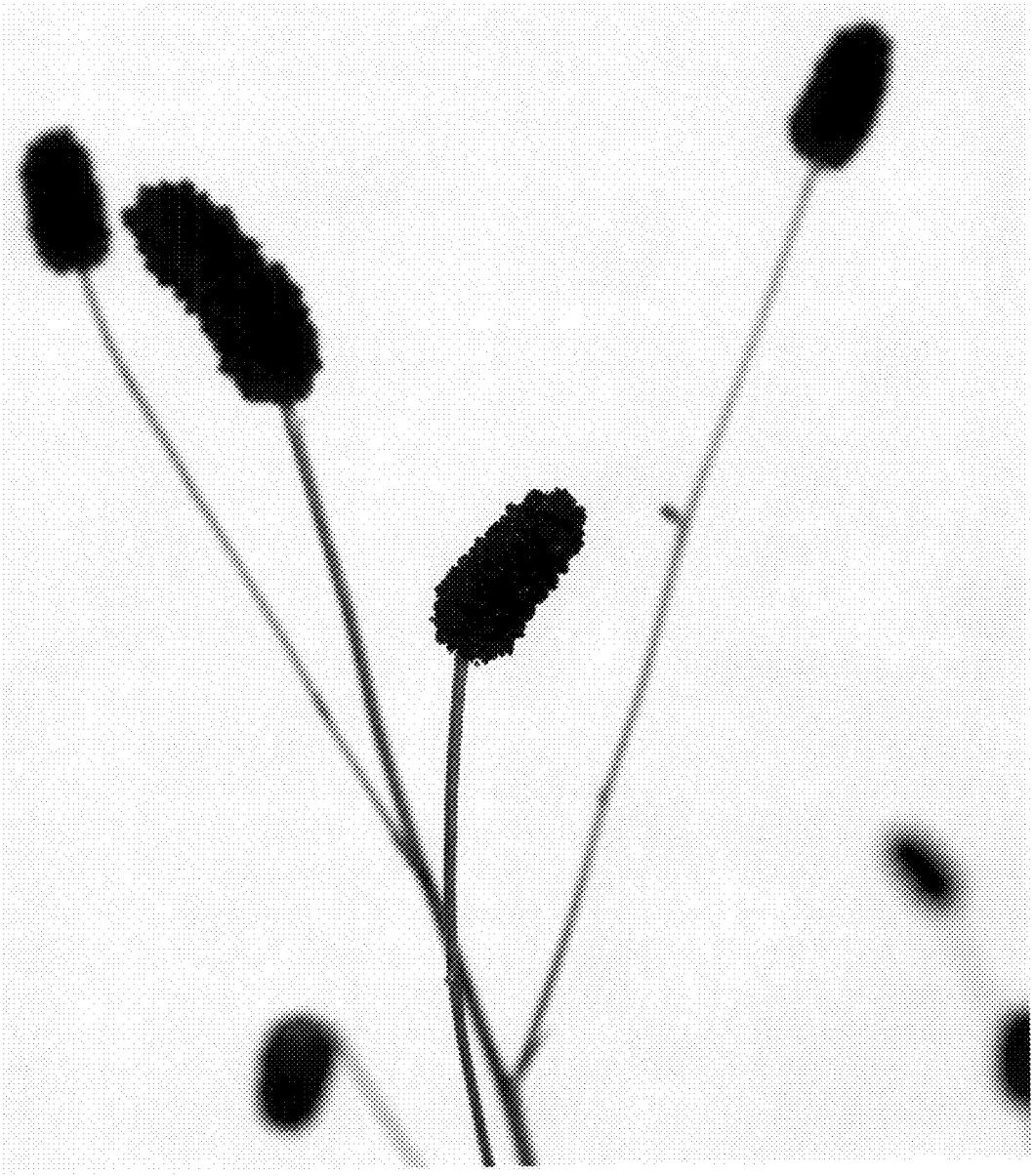

The photograph in FIG. 2 provides a close-up view of the inflorescences of 'Black Dream Select'.

Figure 3:
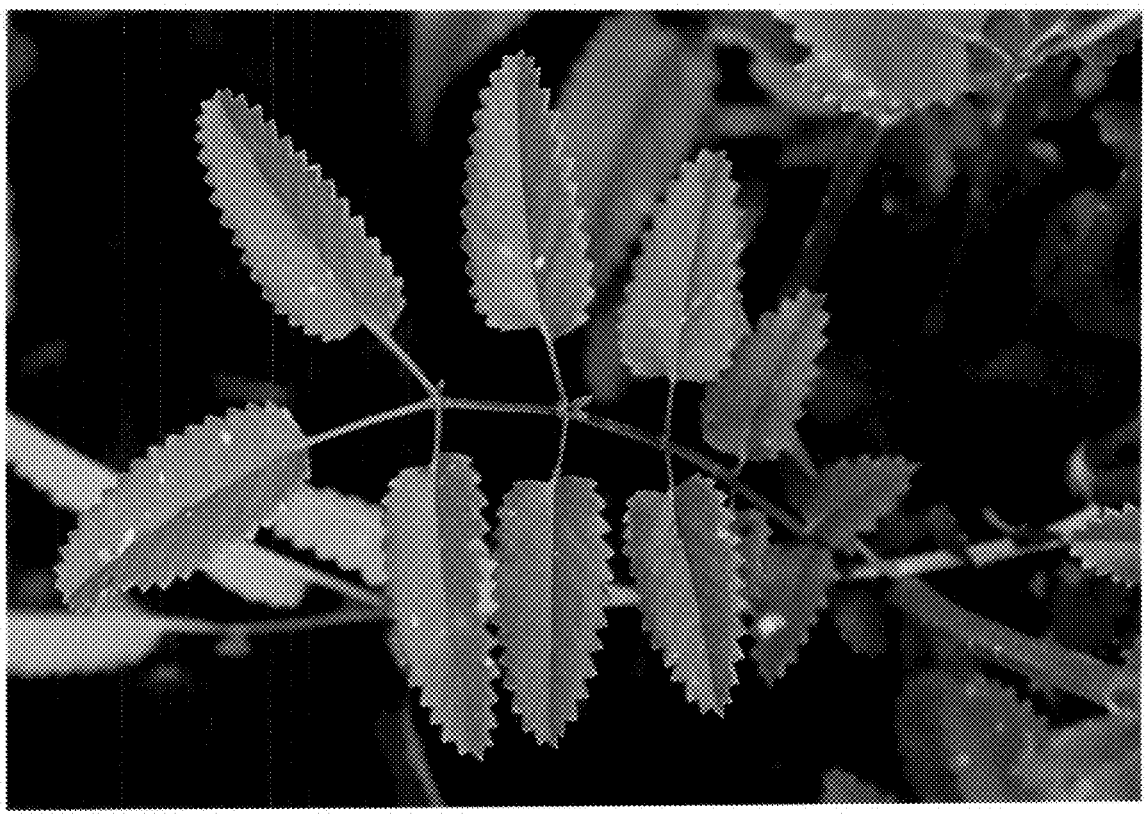

The photograph in FIG. 3 provides a close-up view of the foliage of 'Black Dream Select'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with the 2015 $6^{th}$ edition (2019 reprint) Colour Chart of The Royal Horticultural Society, London, England, except where general color terms of ordinary dictionary significance are used.

General description:

*Blooming period*.—July through August in The Netherlands.

*Plant habit*.—Herbaceous perennial.

*Height and spread*.—Average of 87.5 cm in height from soil level to top of foliar plane, 1.21 m in height from soil level to top of floral plane, 65 cm in spread as a one-year-old field grown plant.

*Hardiness*.—At least in U.S.D.A. Zones 4 to 9.

*Diseases and pests*.—No susceptibility or resistance to diseases or pests has been observed.

*Root description*.—Moderately fibrous, very freely branched, smooth, glabrous with no root hairs, main roots are an average of 3 mm in diameter, 164C in color.

*Time required for root initiation*.—An average of 2 to 4 weeks.

*Time required to produce a young plant from a rooted cutting*.—An average of 4 to 5 months.

*Propagation*.—Division.

*Growth rate*.—Vigorous.

Stem description:

*Shape*.—Round, moderately angled.

*Stem color*.—Young; 138A, mature; 144A.

*Stem size*.—86.4 cm in length and 3.5 mm in diameter.

*Stem aspect*.—Average of 10° to vertical.

*Stem surface*.—Slightly glossy.

*Stem strength*.—Strong.

*Internode length*.—16.3 cm.

*Branching*.—Main; 13, lateral; 10.

Foliage description:

*Leaf shape*.—Oblong.

*Leaf division*.—Compound; an average of 9 leaflets per leaf (ranges from 13 leaflets on the lower leaves to 5 leaflets on the upper leaves).

*Leaf base*.—Truncate.

*Leaf aspect*.—Outward.

*Leaf arrangement*.—Alternate.

*Leaf size*.—Average of 16.4 cm in length (including petiole), 7.6 cm in width.

*Leaf attachment*.—Petiolate.

*Leaflet*.—Narrow ovate to lanceolate in shape, top leaflets; average of 3.6 cm in length, 1.5 cm in width, lateral leaflets; average of 3.4 cm in length and 1.5 cm in width, acute apex, truncate to attenuate base.

*Leaflet venation*.—Pinnate, upper surface color 138B, lower surface 1476D.

*Leaflet margins*.—Dentate-crenate to dentate-serrate.

*Leaflet surface*.—Both surfaces smooth and glabrous, upper surface slightly glossy, lower surface matte.

*Leaflet color*.—Young; upper surface 137B, lower surface N138B, mature; upper surface NN137B, lower surface N138B.

*Rachis (petiole) and petiolule*.—Rachis (petiole); average of 11.7 cm in length, 1.5 mm in diameter, petiolule; average of 1.3 cm in length and 0.75 mm in diameter, slightly glossy, smooth and glabrous, strong, upper surface color 143C, tinged 187B to 187C at the leaflet nodes, lower surface color 143C.

*Stipules*.—At the base of each leaf is a leafy stipule on each side, falcate in shape, 1.2 cm in length, 1.6 cm in width, surfaces smooth and glabrous, serrate-dentate margins, color upper surface NN137A, lower surface a color between 138B, at the base of each petiolule a leafy stipule is present on each side, ovate in shape, 8 mm in length, 0.5 mm in width, both surfaces smooth and glabrous, margins shallow dentate-serrate, upper side slightly glossy and 137B in color, lower side 138B in color.

Inflorescence description:

*Type*.—Terminal spikes of numerous, densely packed flowers in elongated ovoid to oblong shaped inflorescence.

*Inflorescence size*.—Panicle; average of 28 cm in height, 31.3 cm in diameter, spike; 2.8 cm in height, 1 cm in diameter.

*Fragrance*.—Moderately strong, woozy, and slightly unpleasant.

*Flower lastingness*.—About 14 days, persistent.

*Flower quantity*.—Average of 175 flowers per spike, over 26,000 flowers and buds per plant.

*Flower aspect*.—Rotate, single, outward and freely flowering.

*Flower size*.—Average of 2.5 mm in height and diameter, 3.5 mm in depth.

*Peduncle*.—Average of 18.4 cm in length, 2 mm in diameter, held straight up, strong, smooth and glabrous, slightly glossy, 143A in color.

*Flower buds*.—Average of 3 mm in length, 1.5 mm in diameter, obovate in shape, smooth, glabrous, and matte surface, color; N186D, axially striped N186C, base 145C and 145D.

*Petals*.—Rotate, cruciform, average of 4, 1 row, unfused, 2 mm in length, 1 mm in width, ovate and slightly concave in shape, acute tip, cuneate base, entire margins, both surfaces glabrous, slightly velvety and matte, color; when opening upper surface; upper half 65A to 65D, centered and tipped 183A, lower half 155C and 157D, when opening lower surface; upper half 65A to 65D, centered and tipped 187B and 187C, lower half 155C and 157D, when fully open upper surface; upper half 65A to 65D, centered and tipped 183A, lower half 155C and 157D, veins 187B and 187C, fading to a blend of N186C to 200A, margins N186D, when fully open lower surface; upper half 65A to 65D, centered and tipped 187B and 187C, lower half 155C and 157D, veins 183A, fading to a blend of N186C to 200A, margins N186D, base 146A.

*Calyx*.—Rotate, cruciform, average of 2 mm in length and diameter.

*Sepal*.—An average of 4 in 1 row, average of 2 mm in length and 0.5 mm in width, elliptic in shape, narrowly acute tip, narrowly cuneate base, entire margins, both surfaces matte and moderately pubescent densely covered with soft short hairs, 0.2 mm in length, 157D in color, color; when opening upper and lower surface 199C fully open upper and lower surface 199C, tips 199A.

*Flower bracts*.—None.

Reproductive organs:

*Gynoecium*.—Pistil: 1, average of 1.25 mm in length, stigma is flattened and club-shaped, 0.3 mm in length and diameter, 71B in color, style; average of 1 mm in length, 71B, base 71D in color, ovary; 195C in color.

*Androecium*.—Stamens; average of 4, filament; 1.25 mm in length, 186B in color, anthers; short kidney shaped, 0.3 mm in length, 0.2 mm in width, pollen; low in quantity, 200A in color.

*Fruit/seed*.—None observed.

It is claimed:

1. A new and distinct cultivar of *Sanguisorba* plant named 'Black Dream Select' as herein illustrated and described.

* * * * *